(12) United States Patent
Borini et al.

(10) Patent No.: US 9,042,075 B2
(45) Date of Patent: May 26, 2015

(54) APPARATUS AND METHOD FOR WATER PROTECTION OF AN ELECTRONIC DEVICE

(71) Applicant: Nokia Corporation, Espoo (FI)

(72) Inventors: Stefano M. Borini, Cambridge (GB); Richard White, Huntingdon (GB); Jani Kivioja, Cambridge (GB); Michael R. Astley, Cambridge (GB); Christopher Bower, Ely (GB)

(73) Assignee: Nokia Technologies Oy, Espoo (FI)

( * ) Notice: Subject to any disclaimer, the term of this patent is extended or adjusted under 35 U.S.C. 154(b) by 178 days.

(21) Appl. No.: 13/783,754

(22) Filed: Mar. 4, 2013

(65) Prior Publication Data

US 2014/0247529 A1  Sep. 4, 2014

(51) Int. Cl.
  *H01H 47/00* (2006.01)
  *H02H 3/20* (2006.01)
  *G01N 27/12* (2006.01)

(52) U.S. Cl.
  CPC .............. *H02H 3/20* (2013.01); *G01N 27/121* (2013.01)

(58) Field of Classification Search
  CPC ........................................................ G05D 9/12
  USPC ........................................................ 361/178
  See application file for complete search history.

(56) References Cited

U.S. PATENT DOCUMENTS

| | | | |
|---|---|---|---|
| 5,606,264 A | 2/1997 | Licari et al. | 324/763 |
| 5,790,046 A | 8/1998 | Blossfeld | 340/825.07 |
| 6,078,792 A | 6/2000 | Phillips | 455/90 |
| 6,603,319 B1 | 8/2003 | Kasahara et al. | 324/696 |
| 7,400,917 B2 | 7/2008 | Wood et al. | 455/575.8 |
| 8,015,872 B2 * | 9/2011 | Zhang | 73/335.02 |
| 2011/0279931 A1 | 11/2011 | Nakamura | 361/42 |
| 2012/0038374 A1 | 2/2012 | Johnson | 324/694 |

OTHER PUBLICATIONS

Chen-Te Hsieh et al., "Water/oil repellency and work of adhesion of liquid droplets on grapheme oxide and grapheme surfaces", Surface & Coatings Technology, vol. 205, pp. 4554-4561, Mar. 4, 2011.
Duy-Thach Phan et al., Effects of oxygen-functional groups on humidity sensor based grapheme oxide thin films, Sensors, 2012 IEEE, pp. 1-4, Oct. 2012.
"NE555 Low Voltage Battery Disconnect Circuit", http://www.gorum.ca/lvdisc.html; Jan. 2013 10 pgs.
"Battery Protection IC for I-Cell Pack S-8241 Series", http://www.sii-ic.com/en/product1.jsp?productID=389&subcatID=5; Jan. 2013, 2 pgs.

\* cited by examiner

*Primary Examiner* — Stephen W Jackson
(74) *Attorney, Agent, or Firm* — Harrington & Smith (57) ABSTRACT

An apparatus comprises a sensor having a sensing film and at least two electrodes; and a plurality of electronic components operably associated with the sensor. The sensing film is configured to provide a signal based on humidity immediately prior to contact with liquid water. The electronic components are configured to provide a change in output voltage to trigger an electronic switch that disconnects an electronic device from a power source.

19 Claims, 8 Drawing Sheets

APPARATUS AND METHOD FOR WATER PROTECTION OF AN ELECTRONIC DEVICE

BACKGROUND

1. Technical Field

The exemplary and non-limiting embodiments disclosed herein relate generally to the protection of electronic devices from water and, more particularly, to an apparatus and method for the protection of battery-powered mobile electronic devices from water.

2. Brief Description of Prior Developments

Various types of systems and devices for protecting electronic devices from water are known. Some devices utilize waterproof encapsulation to inhibit the ingress of water into compartments in which electronic circuitry is located. Other devices employ water detection sensors in which a circuit uses electrodes to detect immersion of the circuit in water. Passive water ingress detectors, such as test strips that change color on exposure to water, are also used by manufacturers of mobile devices to avoid warranty replacement due to water damage caused by users of the mobile devices. Such detectors, however, offer no benefit to the users of the mobile devices. Capacitive sensing devices are also used to measure humidity, but such devices tend to be based on the measurement of changes in dielectric constant values of a polymer or oxide and are therefore relatively slow to respond to changes in humidity.

SUMMARY

The following summary is merely intended to be exemplary and is not intended to limit the scope of the claims.

In accordance with one aspect, an apparatus comprises a sensor comprising a sensing film and at least two electrodes; and a plurality of electronic components operably associated with the sensor. The sensing film is configured to provide a signal based on humidity immediately prior to contact with liquid water. The electronic components are configured to provide a change in output voltage to trigger an electronic switch that disconnects an electronic device from a power source.

In accordance with another aspect, a method comprises providing a sensor comprising a sensing film and at least two electrodes, the sensing film being configured to provide a signal based on humidity immediately prior to contact with liquid water, and a plurality of electronic components operably associated with the sensor; and sensing humidity in an electronic circuit using the sensing film to determine a sensor voltage.

In accordance with another aspect, a non-transitory computer readable storage medium comprises one or more sequences of one or more instructions which, when executed by one or more processor of an apparatus, cause the apparatus at least: sense humidity in an electrical circuit using a sensing film to determine a sensor voltage.

BRIEF DESCRIPTION OF THE DRAWINGS

The foregoing aspects and other features are explained in the following description, taken in connection with the accompanying drawings, wherein.

DETAILED DESCRIPTION OF THE EMBODIMENTS

Portable electronic devices, such as phones, cameras, and the like, can be compromised when brought into contact with water. Accidental water damage accounts for a significant proportion of all portable electronic device failures. The repair of water damage to devices under warranty generally involves labor costs that can add significantly to the costs of replacement materials, which, particularly in less expensive devices, is an unacceptable cost burden.

One exemplary approach to avoid water damage of portable electronic devices is to make the devices "water-proof." Water-proofing involves preventing inhibiting water from coming into contact with electronic circuits within the device. There are several ways in which water-proofing of electronic devices can be achieved, one method being to effectively seal all of the open apertures on the device by using elastomeric seals. Such a method, however, means that the various access for example, USB ports, jack-plug connectors, and the like, are provided with removable seals that a user must remember to replace after use, or the device will still be vulnerable to water ingress.

An alternative method is to use a hydrophobic coating either on the internal surfaces of the device or in some cases over the entire device, such a coating being formulated so as minimize water permeation into the device by reducing capillary effects. However, case of severe wetting conditions (e.g., complete submersion of the device into water or liquids containing substantial amounts of water) such an approach may not be sufficient to completely prevent water ingress since often there are still large open apertures into which water may flow. In such instances, electro-migration may occur at the electronic circuitry. Electro-migration is material transport due to gradual movement of ions in a conductor caused by momentum transfer between conducting electrons and ions that make up the lattice of interconnecting material, the occurrence of which in the electronic circuitry may cause short circuit failure of the electronic device. The hydrophobic coating may facilitate a delay of the effects of electro-migration that occur when water comes into contact with electric fields by covering all the active circuitry with a water repellant barrier layer.

Despite the water repellant barrier, as long as the circuitry remains powered there is a chance that electro-migration will cause a short circuit failure of the device. A system able to disconnect the power source prior to the electronics being damaged by water is therefore highly desirable. However, the circuitry should be configured to avoid unwanted shutdown due to conditions of extreme humidity. Furthermore, such circuitry should also be fast enough to avoid irreversible short-circuit damage.

Exemplary embodiments of a device for the protection of a battery-powered electronic device from water are disclosed herein. The device includes a sensor capable of sensing water in liquid or vapor form based on the measurement of very large time derivative values. The sensor comprises (i) a graphene oxide (hereinafter "GO") thin film and (ii) two or more electrodes in contact with the thin film. An electronic switch is connected to the sensor and to a power source (e.g., the battery) that powers the circuitry in the electronic device. One possible trigger to activate the electronic switch to disconnect the circuitry of the electronic device from the power source may be a measured threshold value of the time derivative of the GO sensor signal.

In the exemplary embodiments of such a device, if the relative humidity suddenly increases up to high values (e.g., up to 90%, or higher than predetermined standard device operating conditions), the value of the electrical impedance of the GO thin film drops exponentially by several orders of magnitude and almost instantaneously. Such an instantaneous response translates into large values of the time derivative of the GO impedance, which makes the electronic switch disconnect the power source from the circuitry of the electronic device prior to the contact the circuitry by liquid water, thereby providing an ultrafast response time with regard to the sensing of water.

The GO can be easily integrated into the sensor as a thin film by, for example, being printed on the power source. For example, the sensor may be integrated into a battery, e.g., by printing the GO film and the electrodes directly on a surface of the battery. In some exemplary embodiments, the film may be less than about 100 nanometers (nm) thick. Due to the two-dimensional nature of GO (which is generally employed in flake form), a GO film having a thickness equal to few atomic layers could be achieved, e.g., by Languir-Blodgett deposition. Other exemplary methods by which the GO film can be formed include, but are not limited to, spray coating and spin coating. By employing such methods, the device can be manufactured at low cost.

In alternate exemplary embodiments, the sensor may comprise materials other than GO, such as graphene oxide, reduced graphene oxide, graphene, functionalized graphene, fluorographene, molybdenite, boron nitride, tungsten disulphide, combinations of the foregoing materials, and the like.

The use of a time derivative threshold as the trigger to activate the electronic switch can accommodate an unusual and potentially harmful situation such as a drastic change of humidity that occurs almost instantaneously (such as, for example, submersion of the electronic device into water). The use of the time derivative threshold as the trigger may also be used to discriminate such a situation from a situation where an electronic device incorporating the sensor is used in an environment simply having a high humidity.

In one exemplary aspect, the device could be implemented in a mobile phone in order to protect the circuitry of the mobile phone in case of contact with water.

Figure 1:
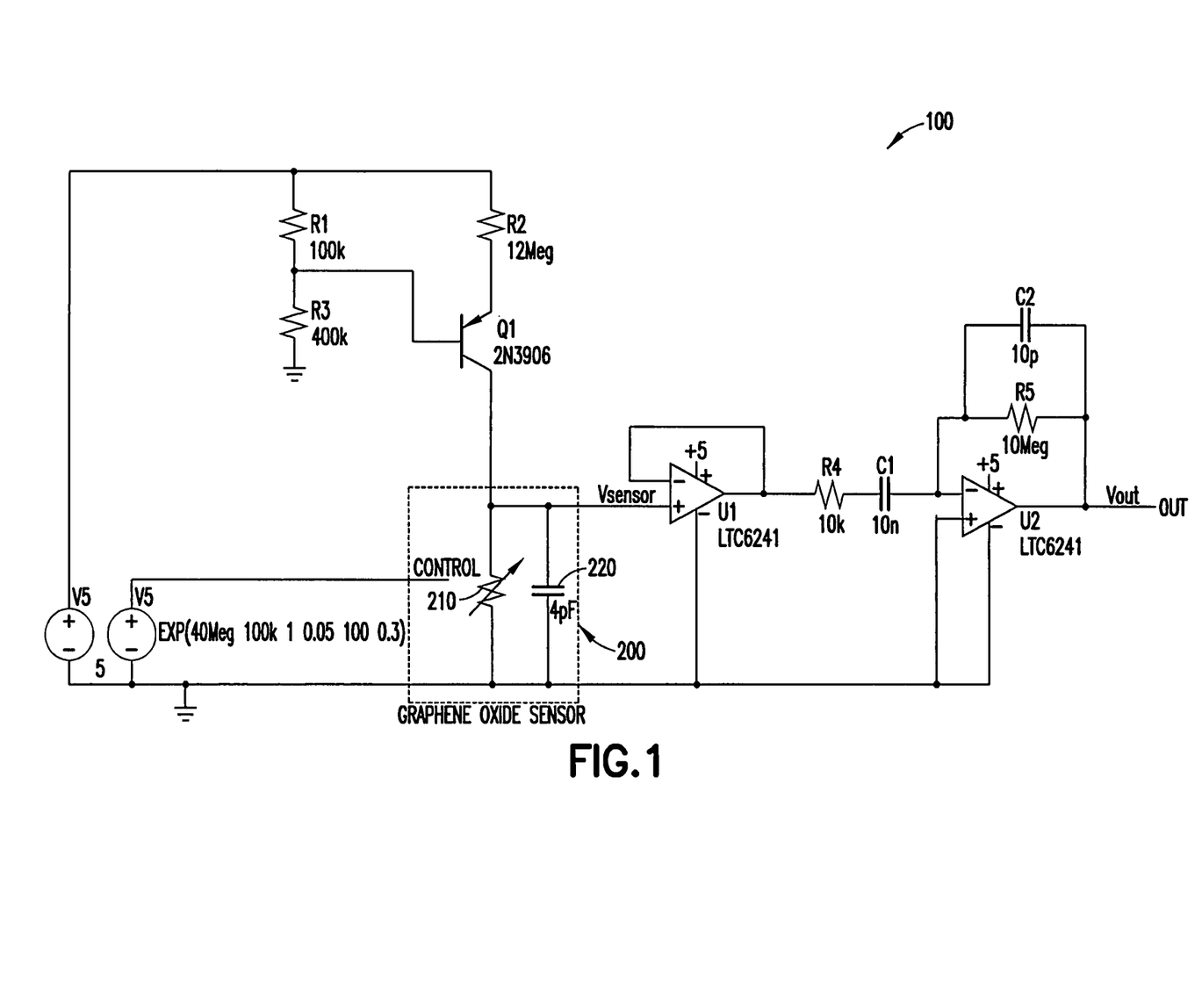
FIG. 1 a schematic circuit diagram of one exemplary embodiment a device for the protection an electronic device from water, the device comprising a sensor comprising a graphene oxide film.

Referring now to FIG. 1, one exemplary system or device for the protection of an electronic device from water is designated generally by the reference number 100 and is hereinafter referred to as "device 100." Device 100 includes the sensor (shown at 200) and associated electronic components, all of which are arranged as a circuit. In the exemplary device as shown, the sensor 200 comprises a thin sensing film defined by layers of GO. In alternate exemplary devices, to sensor 200 may comprise a thin film of other material as indicated above.

The device 100 is configured to measure a signal from the sensor 200 such that sudden increases in humidity (e.g., as caused by dropping the electronic device into water) can be protected against, but such that the protection is not triggered if the electronic device is simply used under ambient conditions in which humidity is relatively high (e.g., in misty weather). The circuit detects and processes the signal, which is based on a variation in electrical impedance of the sensing film. Processing of the signal is performed to measure the time derivative (rate of change of electrical resistance) of the sensor 200. In the exemplary embodiment shown, the device 100 is defined as a circuit that measures a rate of change of the resistance of the GO film. More specifically, the circuit produces an output voltage that is proportional to a rate of change of the electrical resistance of the GO film.

The sensor 200 is modeled with the sensing film (the GO film) shown as a variable resistor 210 in parallel with a 4 picofarad capacitor 220.

With regard to the electronic components associated with the sensor 200, a transistor Q1 provides a constant current source (e.g., about 50 nanoamps (50 nA)) across the sensor 200 such that a sensor voltage ($V_{sensor}$) at the non-inverting input of an amplifier U1 is proportional to the sensor resistance. The amplifier U1 buffers this voltage due to the impedance of the sensor 200. At measurement frequencies of interest (a few Hertz (Hz)), an operational amplifier U2, a capacitor C1, and a resistor R5 produce a differentiating amplifier having an output voltage ($V_{out}$):

$$V_{out} = -R_5 C_1 \frac{dV_{Sensor}}{dt}$$

Also in the device 100, a resistor R4 and a capacitor C2 aid stability of the circuit and remove high-frequency noise.

Figure 2A:
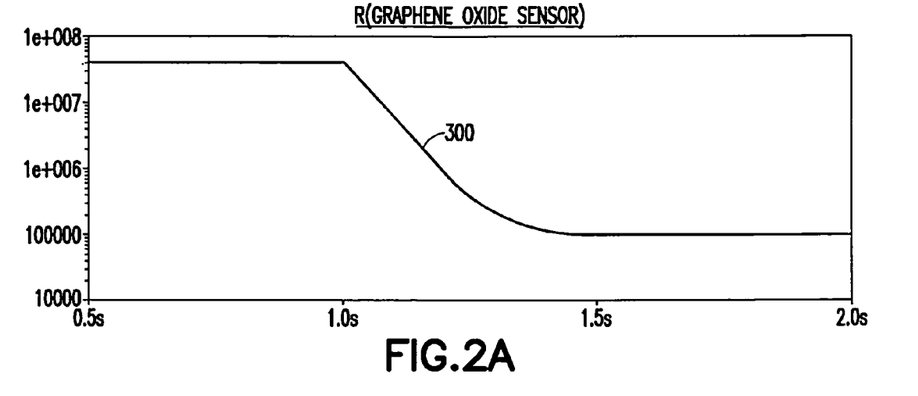
FIG. 2A is a graphical representation of a resistance of the sensor of FIG. 1 as a function of time.
Figure 2B:
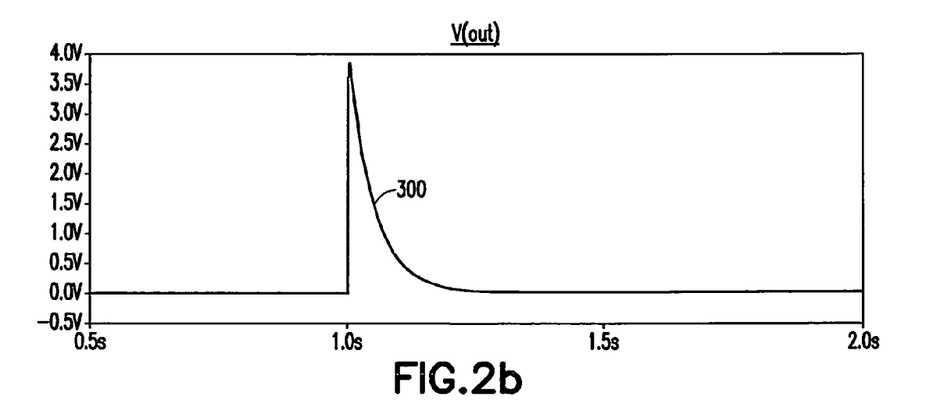
FIG. 2B is a graphical representation of an output voltage of the device of FIG. 1 as a function of time.

Referring now to FIGS. 2A and 2B, during an exemplary operation of the circuit of device 100, after one second, the humidity is suddenly increased, and so the resistance of the sensing film 210 of the sensor 200 decreases exponentially (shown at 300) from 40 mega ohms (MΩ) to 100 kilo ohms (kΩ). This sudden change results in a voltage pulse in the output voltage ($V_{out}$). In one embodiment, the sudden change may be indicated by the normalized derivative R'/R (where R' is the time derivative dR/dt and R is the resistance) as the parameter to indicate a threshold value (e.g., about 5 s$^{-1}$ to about 15 s$^{-1}$). In the event of an electronic device incorporating device 100 being dropped in water, the voltage pulse occurs a substantial amount of time before water ingress is able to cause short circuits in the electronic components of the circuit, which could adversely affect the electronic device. In FIG. 2A, the resistance the sensor 200 is shown as a function of time. In FIG. 2B, the output voltage ($V_{out}$) of the circuit is shown as a function of time.

In some embodiments, output voltage ($V_{out}$) can be used either to drive a latching relay which, when triggered, removes power to circuits of an electronic device (such as mobile phone), or it could be attached to digitally controlled switch incorporating a TTL (transistor-transistor logic input or CMOS (complementary metal oxide semiconductor) logic input to trigger more sophisticated power-down routines. In other embodiments in which increased control of the trigger value is exercised, the output voltage ($V_{out}$) could also be used to drive a comparator.

In some exemplary embodiments, a hydrophobic nano-coating may be deposited on the electrodes to enhance the selectivity of the sensor 200 to water ingress. The material of this coating may be the same hydrophobic material that can be used as a film to coat outer surfaces of the electronic device for water protection, exemplary embodiments of such hydrophobic materials including, but not being limited to, oleofins, fluorinated materials, and other oleophobic surfaces. In an exemplary embodiment employing a hydrophobic nanocoating, a measure of water penetration through the coating may be possible and may allow more distinction between high humidity environments and actual water ingress. The sensitivity of the sensor 200 can be tuned by changing the thickness and/or porosity of the coating and/or the type of hydrophobic material that is used. In some embodiments, a polymeric coating might be used with a certain ratio of carbon to fluorine atoms. By tuning the degree of fluorination of the polymer, the degree of water resistance can be increased or decreased so that a prescribed level of humidity associated with water ingress causes switching, while lower levels of humidity such as might be encountered an ambient environment do not trigger the switch. In some exemplary embodiments, the layer defined by the hydrophobic material may retain some level of porosity to allow the sensor function reliably.

Figure 3A:
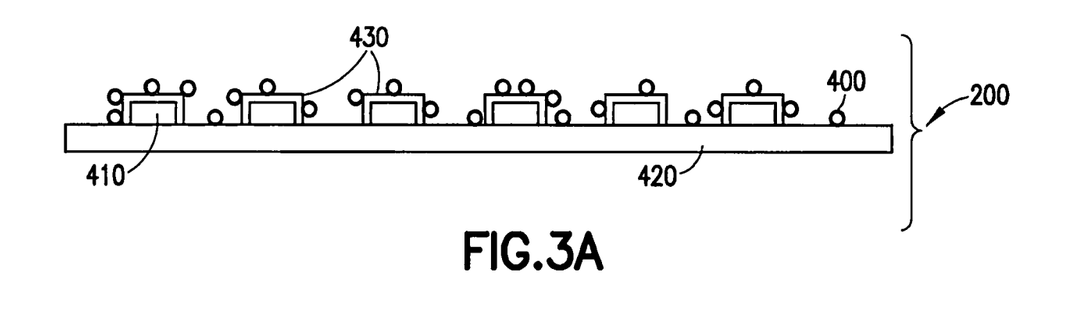
FIG. 3A is a schematic representation of an exemplary configuration of a sensor employing a porous nanostructured coating that creates a super-hydrophobic layer on a surface of the sensor.
Figure 3B:
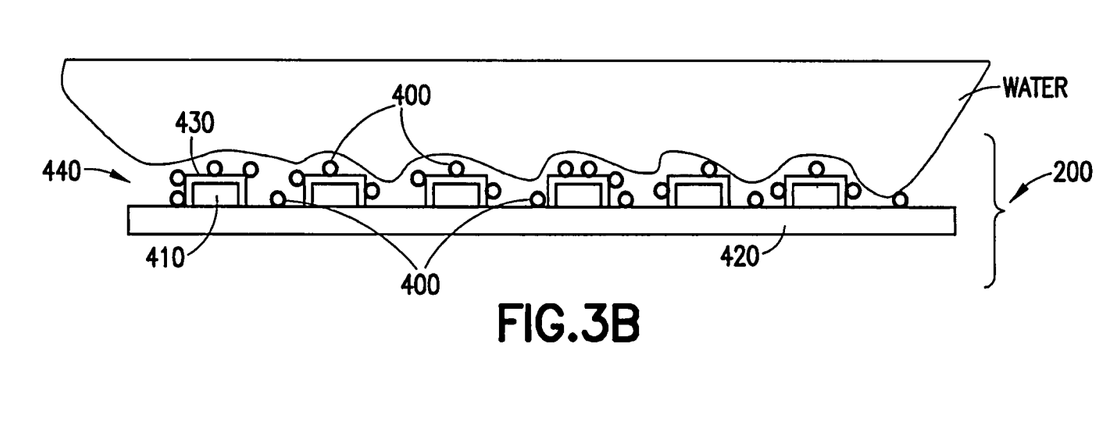
FIG. 3B is a schematic representation of the sensor of FIG. 3A showing a film of air trapped between water and the super-hydrophobic layer.

Referring now to FIGS. 3A and 3B, an alternative exemplary configuration of the coating may be employed to tune the sensitivity of the sensor 200. This alternative exemplary configuration avoids the retention of porosity by employing a porous nanostructured coating 400 that creates a super-hydrophobic layer that traps a film of air on the surface of the sensor 200. In the configuration as shown in FIG. 3A, conducting electrodes 410 are positioned on a substrate 420, and coatings 430 of GO are deposited or otherwise disposed on the conducting electrodes 410. The porous nanostructured coating 400, which is defined by discrete particles of material, is deposited on the coatings 430 of GO.

The nanostructured coating 400 is formed and treated so as to be hydrophobic, so that the material thereof repels water/water-based liquids. Such material includes, for example, oleofins, fluorinated materials, and other oleophobic surfaces). The nanostructured coating 400 can be made by the spraying of hydrophobic silica nanoparticles from solutions of volatile solvent, or directly flame-spraying inorganic hydrophobic silica or alumina nanoparticles which can be rendered superhydrophobic by controlled exposure with a fluoroalkylsilane material (though other chemical treatments are possible). This results in a lowering of the surface energy of the nanostructured layer which further results in the surface having a large advancing contact angle for water of about 145 degrees, and similarly large receding contact angle, resulting in low contact angle hysteresis (water drops can be seen to readily slide off such surfaces). The non-structured layer can also be created by the spray coating of fluorinated polymer materials having a large ratio of fluorine to carbon atoms, e.g., polytetrafluoroethylene (PTFE) or similar material.

As shown in FIG. 3B, the material of the nanostructured coating 400 is super-hydrophobic so as to trap a film 440 of air on the surface of the sensor 200 such that water is substantially prevented (or at least inhibited) from coming into contact with the sensor surface, and yet the GO is still to ambient conditions, thereby allowing for humidity measurement while preventing water contact with the sensor 200.

EXAMPLE 1

Figure 4A:
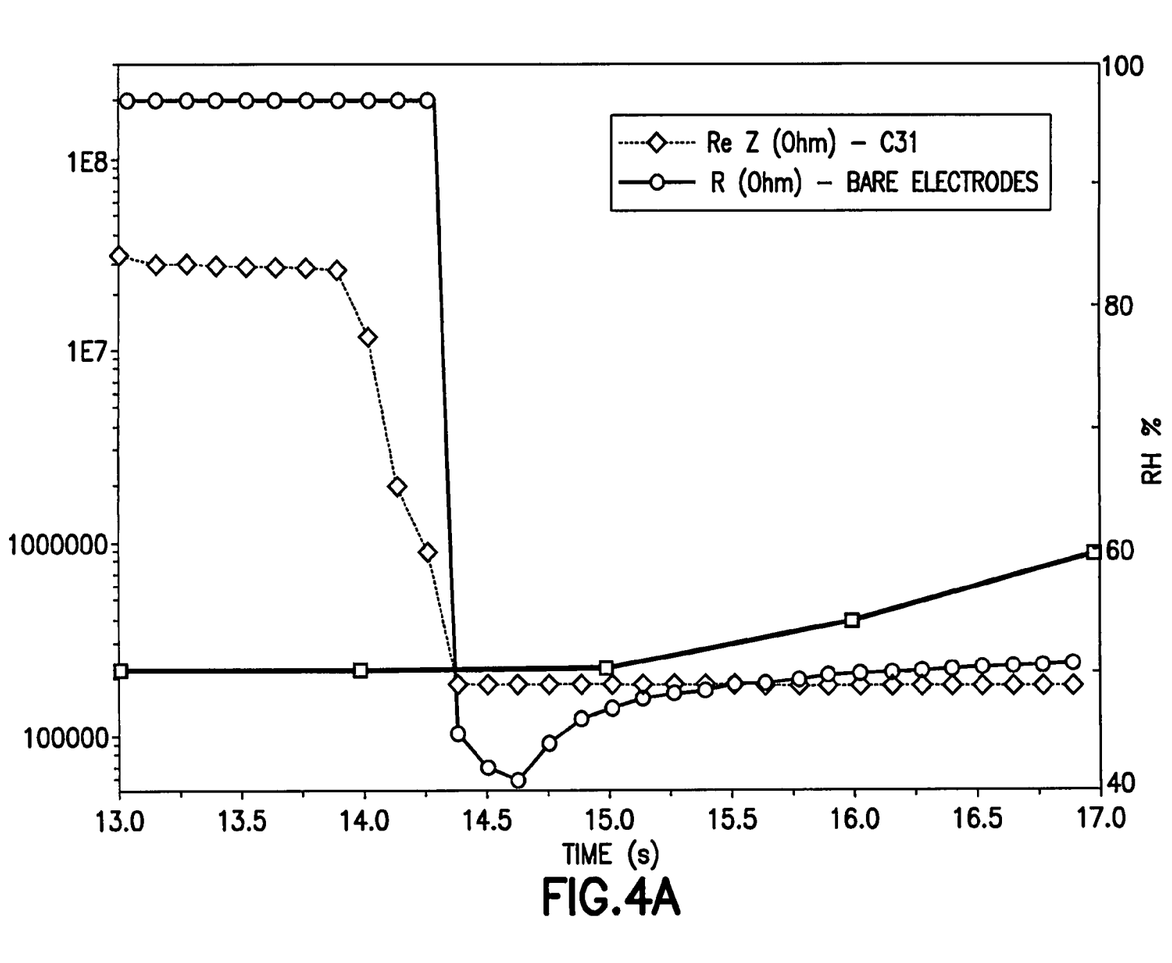
FIG. 4A is a graphical representation of responses of various sensors characterized by resistance values as functions of time.
Figure 4B:
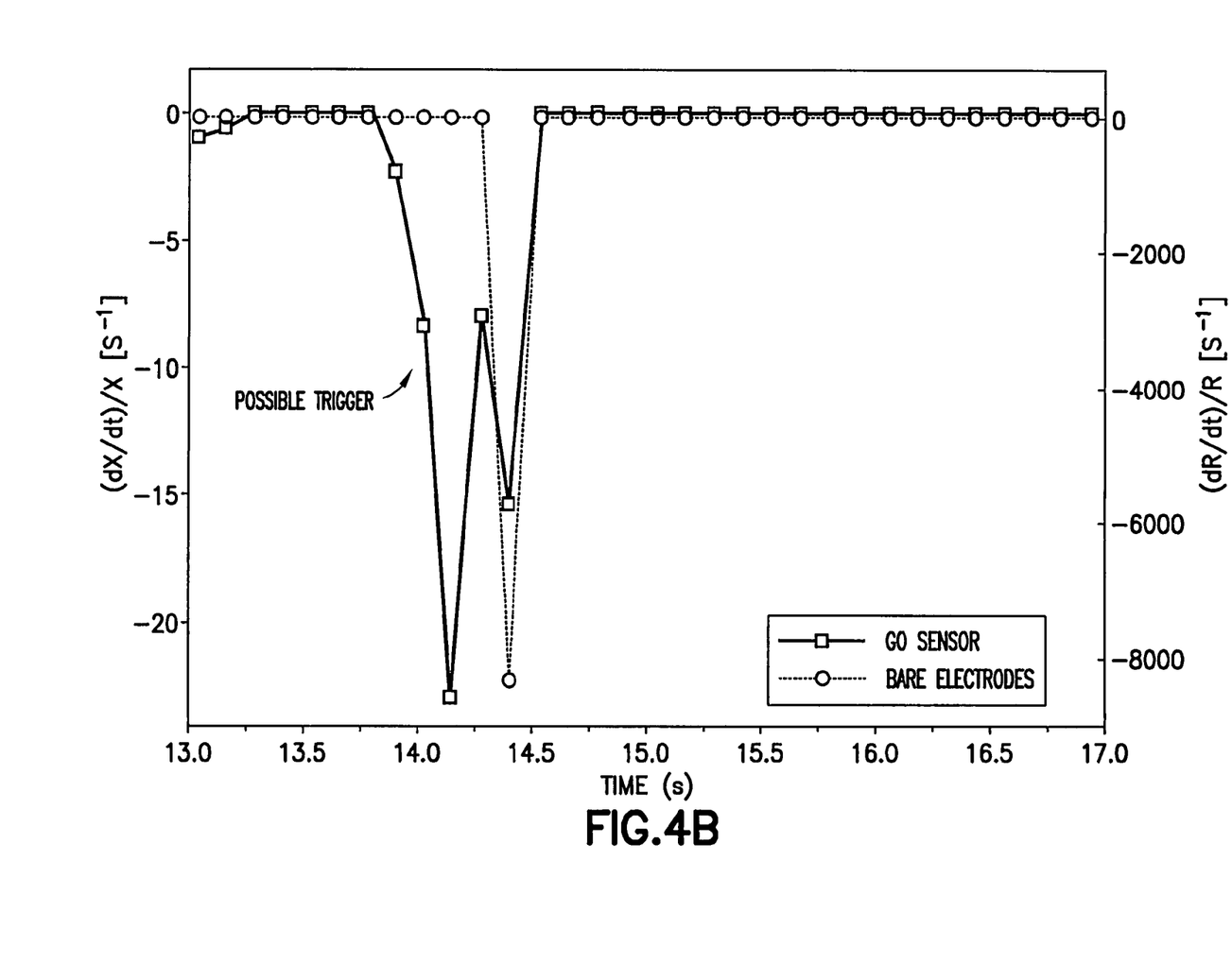
FIG. 4B is a graphical representation of normalized time derivatives of the responses of the sensors of FIG. 4A.

In one example, the sensor 200 was configured to provide a switch-off trigger prior to complete submersion of the electronic device where a commercial humidity sensor and a sensor comprising "bare electrodes" were not able to do so. In such a configuration, the sensor 200 comprising GO was mounted within a battery cavity of a mobile phone (not encased in a water-proof container) along with a commercial humidity sensor that utilized analog and digital signal processing and a "bare electrodes" sensor. The mobile phone was suddenly and almost instantaneously submerged in water. FIG. 4A shows the response of each sensor as a function of time. FIG. 4B shows a normalized time derivative of the responses of the sensor 200 comprising GO and the "bare electrodes" sensor as shown in FIG. 4A. As can be seen in FIGS. 4A and 4B, the switch-off trigger was provided in the case of water submersion of the device. Upon submersion the mobile phone, results pertaining to whether the switch-off trigger could be provided in the case a sudden change of relative humidity in the environment were inconclusive. As indicated in FIG. 4B, one exemplary threshold value of the normalized derivative indicating a sudden change in relative humidity as measured by the sensor 200 was about 10 $s^{-1}$.

EXAMPLE 2

In an effort to assess the ability of the switch-off trigger to be provided in the case of sudden change of relative humidity in the environment, as could be experienced by a user leaving an air-conditioned building in humid weather, the same mobile phone with the sensors within the battery cavity was enclosed in an inner chamber within an outer chamber. The outer chamber was configured to simulate environmental conditions by being kept at greater than 95% relative humidity. The mobile phone was then suddenly exposed to this high relative humidity environment by opening the inner chamber.

Figure 5:
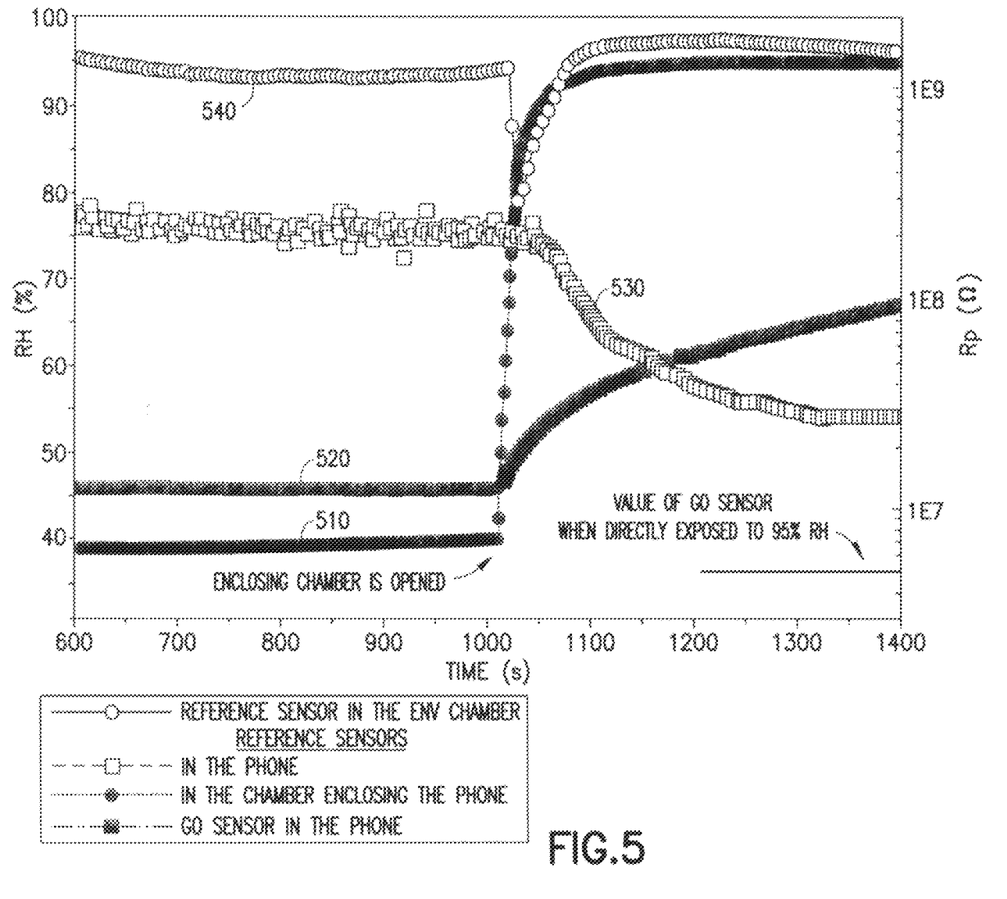
FIG. 5 is a graphical representation of a response or graphene oxide film sensor to a sudden increase in relative humidity.

FIG. 5 shows that the humidity within the mobile phone varied slowly and that no instantaneous response of sensor 200 comprising GO was detected (i.e. no switch-off trigger was provided). As shown in FIG. 5, upon opening the inner chamber at t=1000 seconds, the humidity in the inner chamber rapidly increased, as indicated by line 510. In doing so, the commercial humidity sensor utilizing analog and digital signal processing showed a corresponding increase in relative humidity, as indicated by line 520. The exemplary sensor 200 incorporating the GO film, accordingly, decreased in resistance, as indicated by line 530. A reference electrode placed in the outer chamber showed a dip, as indicated by line 540, due to the opening of the outer chamber in order to access and open the inner chamber.

Figure 6A:
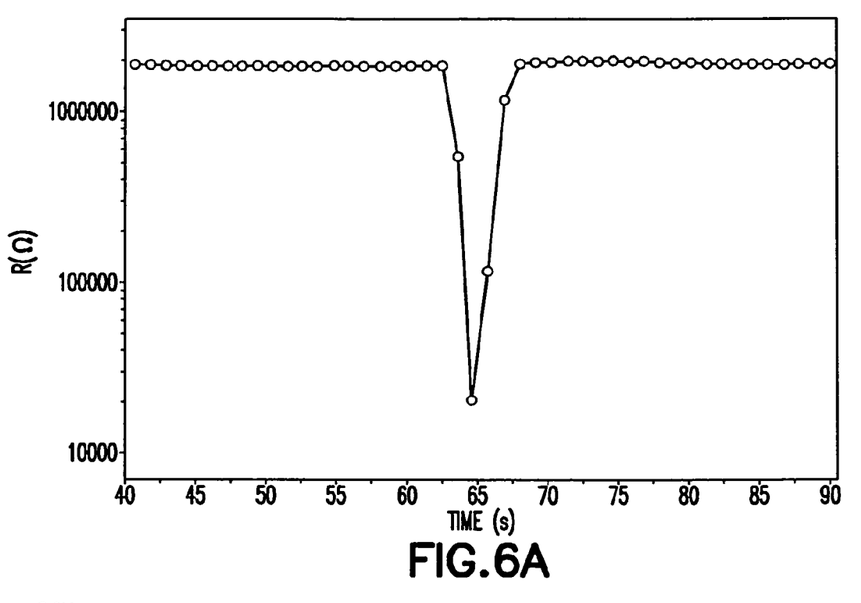
FIG. 6A is a graphical representation of a response of the resistance of a GO film at a frequency of 10 kHz to a high humidity pulse.
Figure 6B:
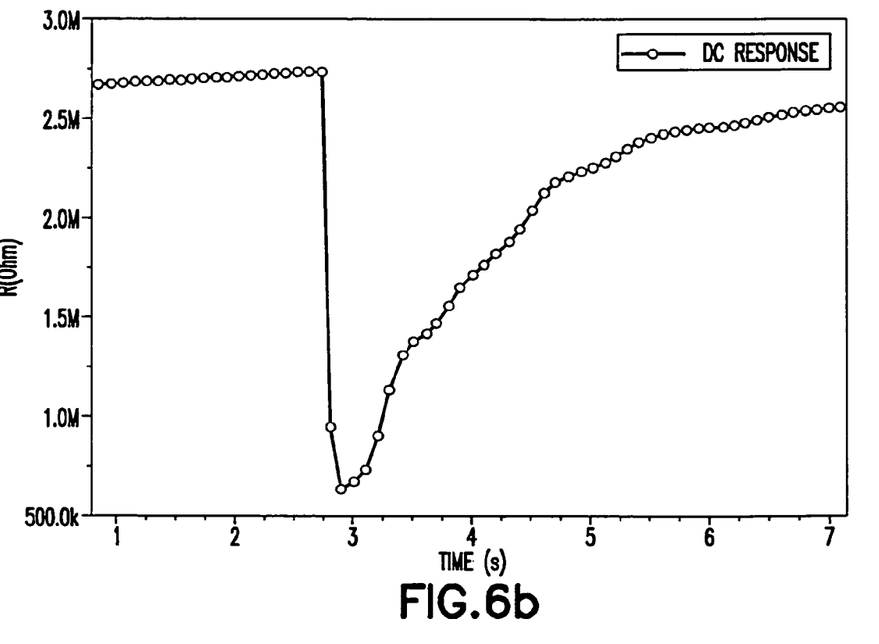
FIG. 6B is a graphical representation of a response of the resistance of a GO film at direct current to a high humidity pulse.

In the exemplary embodiments of the sensor 200 as disclosed herein, sensors comprising thin films of GO can show an ultrafast response to exposure to relative humidity. As shown in FIG. 6A, response of the resistance at 10 kHz as a function of time is shown. As shown in FIG. 6B, a response of the resistance at direct current of a GO thin film to a high humidity as a function of time is shown.

Figure 7:
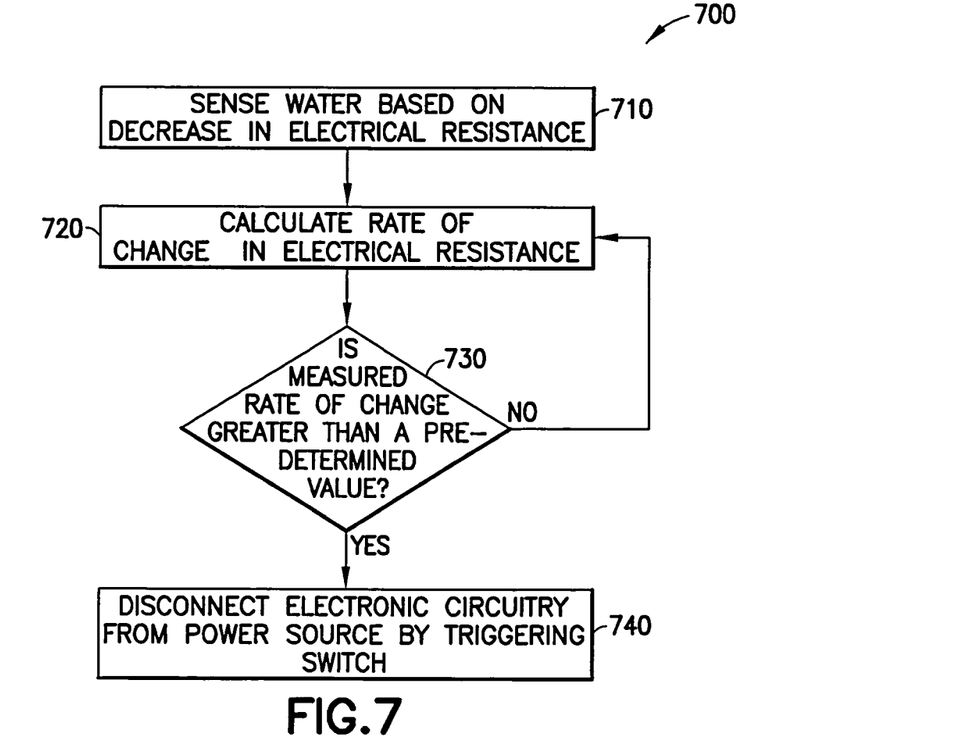
FIG. 7 is a diagram illustrating one exemplary method of using the device embodied by the circuit diagram of FIG. 1.

Referring now to FIG. 7, one exemplary method of disconnecting an electronic device from a power source prior to an actual presence of water on the circuitry of the electronic device is designated generally by the reference number 700 and is hereinafter referred to as "method 700." Method 700, which may be defined by software and embodied on a non-transitory storage medium of a computer, comprises a sensing step 710 in which water is sensed based on a decrease in electrical resistance at the sensing film 210 of the sensor 200. In sensing the water based on electrical resistance, a first value of the sensor voltage ($V_{sensor}$), which is proportional to the value of resistance of the sensing film 210, is determined and stored in a memory. A second sensor voltage ($V_{sensor}$) is then determined. Any suitable clock function may be used to record and store (in the memory) the elapsed time between the first sensor voltage ($V_{sensor}$) and the second sensor voltage ($V_{sensor}$).

A calculating step 720 is then carried out in which the output voltage ($V_{out}$) from the differentiating amplifier is calculated based on the change in sensor voltage ($V_{sensor}$) in conjunction with the resistor R5 and the capacitor C1.

A comparison step 730 is then carried out. In the comparison 730, a determination is made as whether the output voltage ($V_{out}$) exceeds a predetermined value. If the output voltage ($V_{out}$) does not exceed the predetermined value, control is passed back to the measuring step 720 for recalculation of the output voltage ($V_{out}$). If, however, the output voltage ($V_{out}$) does exceed the predetermined value, then control is passed to a disconnect step 740 in which the electronic switch is triggered and power to the circuit of the electronic device is interrupted. As stated above, if the output voltage ($V_{out}$) is in excess of the predetermined value, the output voltage ($V_{out}$) can be used to drive a latching relay or used to trigger power-down routines through TTL or CMOS inputs.

The exemplary embodiments of the apparatuses and methods pertaining to the sensor as disclosed herein can be advantageously considered complementary to other apparatuses and methods that prevent water damage of a mobile electronics device by water-proof encapsulation. Furthermore, the exemplary embodiments as disclosed herein may be used without specialized water-proof containers for a particular mobile electronics device, could be easily integrated with other mobile electronics devices at low cost, and could increase the lifetime of a mobile electronics device while reducing costs due to warranty claims for water damage. Moreover, the exemplary embodiments as disclosed herein could improve the robustness of mobile electronics devices and reduce chances of water damage occurring, thereby improving brand perception and trust.

In one example, an apparatus comprises sensor having a sensing film and at least two electrodes and a plurality of electronic components operably associated with the sensor. The sensing film configured to provide signal based on humidity immediately prior to contact with liquid water. The electronic components are configured to provide a change in output voltage to trigger an electronic switch that disconnects an electronic device from a power source.

In still another example, a method comprises providing a sensor comprising a sensing film and at least two electrodes, the sensing film being configured to provide a signal based upon humidity immediately prior to contact with liquid water, and a plurality of electronic components operably associated with the sensor; and sensing humidity in an electrical circuit using the sensing film to determine a sensor voltage.

In still another example, a non-transitory computer readable storage medium comprises one or more sequences of one or more instructions which, when executed by one or more processors of an apparatus, cause the apparatus to at least: sense humidity in an electrical circuit using a sensing film to determine a sensor voltage.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications, and variances which fall within the scope of the appended claims.

What is claimed is:

1. An apparatus, comprising:
a sensor comprising a sensing film and at least two electrodes, the sensing film being configured to provide a signal based on a change of electrical resistance immediately prior to contact with liquid water humidity; and
a plurality of electronic components operably associated with the sensor, where the electronic components are configured to provide a change in output voltage to trigger an electronic switch that disconnects an electronic device from a power source;
wherein the sensing film comprises graphene oxide.

2. The apparatus of claim 1, where the sensing film further comprises a material selected from the group consisting of reduced graphene oxide, graphene, functionalized graphene, fluorographene, molybdenite, boron nitride, tungsten disulphide, and combinations of the foregoing materials.

3. The apparatus of claim 1, where the signal based upon a change of electrical resistance is a variation in electrical impedance of the sensing film.

4. The apparatus of claim 3, where the variation in electrical impedance is a rate of change of electrical resistance of the sensor.

5. The apparatus of claim 4, where the rate of change of electrical resistance of the sensor is proportional to the change in output voltage of the electronic components.

6. The apparatus of claim 5, where the output voltage is produced by a differentiating amplifier defined by at least a portion of the electronic components.

7. The apparatus of claim 1, where the electronic switch that disconnects the electronic components from the power source is a latching relay or a digitally controlled switch.

8. The apparatus of claim 1, further comprising a hydrophobic coating on the electrodes.

9. The apparatus of claim 8, where a thickness of the hydrophobic coating on the electrodes is tuned to vary a sensitivity of the sensor.

10. The apparatus of claim 9, where the hydrophobic coating is tuned by changing one or more of a thickness of the hydrophobic coating, a porosity of the hydrophobic coating, and a type of material used for the hydrophobic coating.

11. The apparatus of claim 9, where the hydrophobic coating is tuned by varying a ratio of fluorine atoms to carbon atoms.

12. The apparatus of claim 8, where the hydrophobic coating is a porous nanostructured coating that traps a film of air on a surface of the sensor.

13. A method, comprising:
providing a sensor comprising a sensing film comprising graphene oxide and at least two electrodes, the sensing film being configured to provide a signal based upon a change of electrical resistance immediately prior to contact with liquid water, and a plurality of electronic components operably associated with the sensor; and sensing humidity in an electrical circuit using the sensing film to determine a sensor voltage.

14. The method of claim 13, further comprising,
calculating an output voltage based on a change in sensor voltage,
comparing the output voltage to a predetermined value, and
based on a result of comparing the output voltage to the predetermined value, either recalculating the output voltage or disconnecting an electronic switch to interrupt power from a power source to an electronic device.

15. The method of claim 14, where sensing humidity in an electrical circuit comprises determining a first value of the sensor voltage and determining a second value of the sensor voltage.

16. The method of claim 14, where calculating the output voltage based on the change in sensor voltage is carried out by a differentiating amplifier.

17. The method of claim 14, where disconnecting the electronic switch to interrupt power from the power source to the electronic device comprises one of driving a latching relay, powering the electronic device down based on a TTL input, and powering the electronic device down based on a CMOS input.

18. The method of claim 13, where the sensing film further comprises a material selected from the group consisting of reduced graphene oxide, graphene, functionalized graphene, fluorographene, molybdenite, boron nitride, tungsten disulphide and combinations of the foregoing materials.

19. A non-transitory computer readable storage medium, comprising one or more sequences of one or more instructions which, when executed by one or more processors of an apparatus, cause the apparatus to at least:
sense humidity in an electrical circuit using a sensing film comprising graphene oxide and being configured to provide a signal based on a change of electrical resistance immediately prior to contact with liquid water humidity to determine a sensor voltage.

* * * * *